US010446267B2

(12) United States Patent
Fuhrmann

(10) Patent No.: US 10,446,267 B2
(45) Date of Patent: Oct. 15, 2019

(54) NETWORKED INBOX

(71) Applicant: Epic Systems Corporation, Verona, WI (US)

(72) Inventor: David E. Fuhrmann, Verona, WI (US)

(73) Assignee: Epic Systems Corporation, Verona, WI (US)

( * ) Notice: Subject to any disclaimer, the term of this patent is extended or adjusted under 35 U.S.C. 154(b) by 176 days.

(21) Appl. No.: 15/443,553

(22) Filed: Feb. 27, 2017

(65) Prior Publication Data

US 2017/0177800 A1 Jun. 22, 2017

Related U.S. Application Data

(63) Continuation of application No. 14/329,222, filed on Jul. 11, 2014, now abandoned, which is a continuation of application No. 12/987,252, filed on Jan. 10, 2011, now Pat. No. 8,812,599.

(51) Int. Cl.
| | |
|---|---|
| *G16H 10/60* | (2018.01) |
| *G16H 80/00* | (2018.01) |
| *H04L 12/58* | (2006.01) |
| *G06F 19/00* | (2018.01) |
| *G06Q 50/24* | (2012.01) |
| *G06Q 50/22* | (2018.01) |
| *G06Q 50/00* | (2012.01) |
| *G16H 40/20* | (2018.01) |
| *G16H 15/00* | (2018.01) |

(52) U.S. Cl.
CPC .......... *G16H 10/60* (2018.01); *G16H 80/00* (2018.01); *H04L 51/046* (2013.01); *H04L 51/28* (2013.01); *G06F 19/324* (2013.01); *G06F 19/328* (2013.01); *G06F 19/34* (2013.01); *G06F 19/3418* (2013.01); *G06F 19/3456* (2013.01); *G06F 19/3475* (2013.01); *G06F 19/3481* (2013.01); *G06Q 50/01* (2013.01); *G06Q 50/22* (2013.01); *G06Q 50/24* (2013.01); *G16H 15/00* (2018.01); *G16H 40/20* (2018.01); *H04L 51/14* (2013.01)

(58) Field of Classification Search
CPC ........ G06Q 50/22; G06Q 50/01; G06Q 50/24; G06Q 10/10; G06Q 10/107; G16H 15/00; G16H 80/00; G16H 10/60; G16H 40/20; G16H 10/20; H04L 51/28; H04L 51/30; H04L 29/1215; H04L 61/1564
See application file for complete search history.

(56) References Cited

U.S. PATENT DOCUMENTS

| 2003/0115280 | A1* | 6/2003 | Quine | ................. | H04L 29/1215 709/207 |
| 2009/0049140 | A1* | 2/2009 | Stoddard | .............. | G06Q 10/107 709/206 |

* cited by examiner

*Primary Examiner* — Joseph D Burgess
(74) *Attorney, Agent, or Firm* — Quarles & Brady LLP

(57) ABSTRACT

A computer-implemented electronic messaging method and system, the method comprising the steps of receiving an electronic message at a first system, the electronic message comprising a healthcare provider type, obtaining contextual information associated with the electronic message at the first system, using the healthcare provider type and the contextual information to identify an intended recipient address for an intended healthcare provider recipient for the electronic message and providing the intended recipient address to facilitate delivery of the electronic message to the intended healthcare provider recipient.

16 Claims, 3 Drawing Sheets

NETWORKED INBOX

CROSS-REFERENCE TO RELATED APPLICATIONS

This application is a continuation of U.S. application Ser. No. 14/329,222, filed Jul. 11, 2014, which is a continuation of U.S. application Ser. 12/987,252, filed Jan. 10, 2011, which issued as U.S. Pat. No. 8,812,599 on Aug. 19, 2014, all of which are incorporated herein by reference.

STATEMENT REGARDING FEDERALLY SPONSORED RESEARCH OR DEVELOPMENT

Not applicable.

BACKGROUND OF THE INVENTION

Field of the Invention

The present invention relates to electronic messaging between two entities and specifically to sending messages from one entity to another that leverages information stored by one of the entities and contextual information associated with the message to identify an intended unknown message recipient.

Description of the Related Art

In the medical industry it is often the case that patients see many different physicians, medical assistants, nurses, specialists, etc., in the course of receiving services. Thus, for instance, a patient may initially consult a primary care physician about an ailment, be referred out for tests and imaging activities to one or several different institutions and be referred to one or more specialists, for additional services. Here, in order to provide optimal service for a patient, all caregivers that provide services to a patient need to be able to easily communicate amongst themselves. One way for caregivers to communicate between themselves is via an electronic messaging system.

Typical electronic messaging systems allow one user to send a message to a second user by addressing the message to a specified address associated with the second user. For example, in an e-mail system, each individual user has their own specific address. The e-mail address is usually in the form of: username@domainname. Thus, a user of GMAIL-.COM with a user name of "john.smith" would have an e-mail address of "john.smith@gmail.com".

It is known that an administrator can establish a single e-mail address that can be routed to a number of different recipients by an e-mail server. For example, a company might have a single customer service e-mail address such as customer.service@company.com. A server associated with the customer service e-mail address forwards messages received at the customer service address to a number of different e-mail accounts of employees responsible for monitoring customer service questions. The message is thus distributed to several customer service employees indiscriminately. The company can then use the customer service e-mail address in its product literature so that questions from customers or the general public can be handled without concerns about changes at the company itself: employee turn over, vacations, etc. Furthermore, the actual recipients of the messages can remain generally unknown to the sender at the time the sender sends the electronic message.

While the single e-mail address concept works well for routing messages to a group of intended recipients, unfortunately there is no easy way to use a similar single e-mail address to route a message to one of a plurality of possible recipients. For instance, in a case where an ear, nose and throat (ENT) specialist intends to route a message to a patient's primary care physician (PCP) and does not know the PCP's name or e-mail address, there is no easy way for the ENT specialist to address an e-mail to a single PCP address and have the messaging system deliver the message to the patient's PCP. Similarly, where a patient's PCP intends to route a message to the patient's ENT specialist and does not know who the specialist is or the specialist's e-mail address, currently there is no way for the PCP to address a message to a single address and have the message automatically delivered to the patient's ENT specialist. This problem is exacerbated in cases where patients are serviced by many different physicians and across unaffiliated entities where familiarity between all caregivers and addressing conventions is highly unlikely.

BRIEF SUMMARY OF THE INVENTION

It has been recognized that even when a message sender does not have enough information or access to information usable to identify an intended recipient of a message and/or the recipient's e-mail address, a system can be set up that can use a short descriptor of the recipient and additional contextual information associated with a message to identify an intended recipient. Here, the short recipient descriptor alone is insufficient for the system to identify the intended recipient address but the short recipient descriptor along with the contextual information is sufficient to identify the recipient address.

For instance, where an ENT specialist is working in a patient's medical record chart when the specialist decides to send an e-mail to the patient's PCP, the specialist may be able to simply fill in PCP in the "To" field of an e-mail template. When PCP is typed into the "To" field, a server may be programmed to identify a PCP associated with the patient that is associated with the currently viewed chart, identify an electronic messaging system address for the PCP and fill in the PCP address automatically. In this case, "PCP" is the short recipient descriptor and the patient identifier operates as the contextual information used along with the recipient descriptor to automatically identify the recipient's address.

In other embodiments, after an e-mail targeting PCP is composed, prior to transmission, a patient identifier may be added to the e-mail in some fashion that identifies the patient associated with the chart accessed when the e-mail was composed. Here, the patient identifier again serves as contextual information associated with the e-mail being composed. Upon receiving the e-mail with the patient identifier, receiving e-mail server may then use the PCP identifier and the patient identifier to identify a PCP associated with the patient, identify an address for the PCP and forward the e-mail message to the intended PCP.

In still other embodiments, after PCP is entered in a "To" e-mail field while a patient chart is being examined by an ENT specialist and prior to transmitting the e-mail, a pre-e-mail may automatically be transmitted to at least a subset of servers including the PCP short recipient identifier and a patient identifier associated with the patient's chart being viewed when PCP was entered in the "To" field. In response, each receiving e-mail server may use the PCP identifier and patient identifier to attempt to identify the patient's PCP. Where a server identifies the patient's PCP address, the server automatically transmits the PCP address back to the specialist's e-mail server. The specialist's e-mail server then can either automatically fill in the PCP address in the "To"

field, associate the PCP address with the "To" field or provide an option for the specialist to select the PCP address to fill in the "To" field.

In other embodiments, where a specialist fills "PCP" into a "To" field and then transmits an e-mail prior to the PCP address being resolved, if a receiving e-mail server cannot resolve a unique intended recipient using the PCP descriptor and other contextual information, the server may respond with either an error message or, in the case where two or a small subset of possible intended recipients is resolvable, may provide a list of possible intended recipients for the specialist to choose from. When a list of possible intended recipients is presented and one is selected, the e-mail is then delivered to the selected recipient.

In still other embodiments it is contemplated that contextual information may be gleaned from some part of an e-mail as opposed to being obtained from a currently viewed patient's chart. For instance, it may be required practice for a physician to enter a unique patient identifier in a "Re" line of an e-mail when communicating with another physician about a patient. In this case, the patient identifier (i.e., the contextual information) required to identify a patient's PCP may be gleaned from the "Re" line of an e-mail and used to resolve an intended recipient. Contextual information may be gleaned from other locations as well. In other embodiments patient information may be added to an attachment or the like associated with and transmitted with other e-mail information.

Some embodiments include a computer-implemented electronic messaging method comprising the steps of receiving an electronic message at a first system, the electronic message comprising a caregiver type, obtaining contextual information associated with the electronic message at the first system, using the caregiver type and the contextual information to identify an intended recipient address for an intended caregiver recipient for the electronic message and providing the intended recipient address to facilitate delivery of the electronic message to the intended caregiver recipient.

In some cases the step of obtaining contextual information associated with the electronic message includes obtaining a patient identifier identifying a patient associated with the electronic message. In some cases the step of obtaining a patient identifier includes obtaining the patient identifier from a patient chart.

In some cases the step of obtaining the patient identifier from a patient chart includes obtaining the patient identifier from a patient chart most recently accessed by a caregiver composing the electronic message. In some cases the step of obtaining a patient identifier includes gleaning the identifier from information in the electronic message.

In some cases the step of using the caregiver type and the contextual information to identify an intended recipient address for an intended caregiver recipient for the electronic message includes the steps of associating a patient chart with the electronic message, identifying a caregiver of the caregiver type indicated in the patient chart and identifying an electronic address for the identified caregiver. In some cases the step of receiving an electronic message at a first system includes composing the electronic message at a second system where the electronic message specifies the caregiver type and includes the contextual information and transmitting the electronic message to the first system. In some cases the step of receiving an electronic message at a first system includes receiving the electronic message as the message is entered and prior to transmission of the electronic message. In some cases the electronic message is composed using the first system.

In some cases the electronic message is composed using a second system separate from the first system and wherein the step of receiving the electronic message includes receiving the electronic message from the second system at the first system. In some cases the caregiver type is selected from the group consisting of: doctor, pediatrician, primary care physician, radiologist, specialist, pharmacist, and surgeon. In some cases the caregiver type is a generic type.

In some cases the step of providing the intended recipient address includes automatically inserting the intended recipient address in an address field in the electronic message. In some cases the step of providing the intended recipient address includes presenting the intended recipient address for selection as a target address for the electronic message.

Other embodiments include a networked messaging system comprising a first medical record system comprising patient records and caregiver records and a first computer system communicatively linked to the first medical record system, the first computer system programmed to perform the steps of receiving an electronic message, the electronic message comprising a caregiver type, obtaining contextual information associated with the electronic message, using the caregiver type and the contextual information to identify an intended recipient address for an intended caregiver recipient for the electronic message and providing the intended recipient address to facilitate delivery of the electronic message to the intended caregiver recipient.

In some cases the system is programmed to perform the step of obtaining contextual information associated with the electronic message by obtaining a patient identifier identifying a patient associated with the electronic message. In some cases the system is programmed to perform the step of obtaining a patient identifier by obtaining the patient identifier from a patient chart. In some cases the system is programmed to perform the step of obtaining the patient identifier from a patient chart by obtaining the patient identifier from a patient chart most recently accessed by a caregiver composing the electronic message.

In some cases the system is programmed to perform the step of obtaining a patient identifier by gleaning the identifier from information in the electronic message. In some cases the system is programmed to perform the step of using the caregiver type and the contextual information to identify an intended recipient address for an intended caregiver recipient for the electronic message by associating a patient chart with the electronic message, identifying a caregiver of the caregiver type indicated in the patient chart and identifying an electronic address for the identified caregiver. In some cases the system is programmed to perform the step of receiving an electronic message at a first system by receiving the electronic message from a second system used to compose the electronic message where the electronic message specifies the caregiver type and includes the contextual information.

In some cases the system is programmed to perform the step of receiving an electronic message at a first system by receiving the electronic message as the message is entered and prior to transmission of the electronic message. In some cases the electronic message is composed using the first system. In some cases the electronic message is composed using a second system separate from the first system and wherein the step of receiving the electronic message includes receiving the electronic message from the second system at the first system. In some cases the caregiver type is selected from the group consisting of: doctor, pediatrician, primary care physician, radiologist, specialist, pharmacist, and surgeon.

In some cases the step of providing the intended recipient address includes automatically inserting the intended recipient address in an address field in the electronic message. In some cases wherein the step of providing the intended recipient address includes presenting the intended recipient address for selection as a target address for the electronic message.

Still other embodiments include a computer-implemented electronic messaging method, the method comprising the steps of receiving a general recipient descriptor at a first system where the general recipient descriptor is associated with an electronic message and the general recipient descriptor is descriptive of a plurality of different possible intended message recipients, obtaining contextual information associated with the electronic message, using the general recipient descriptor and the contextual information to identify an intended message recipient address; and providing the intended message recipient address to facilitate delivery of the electronic message to the intended message recipient.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
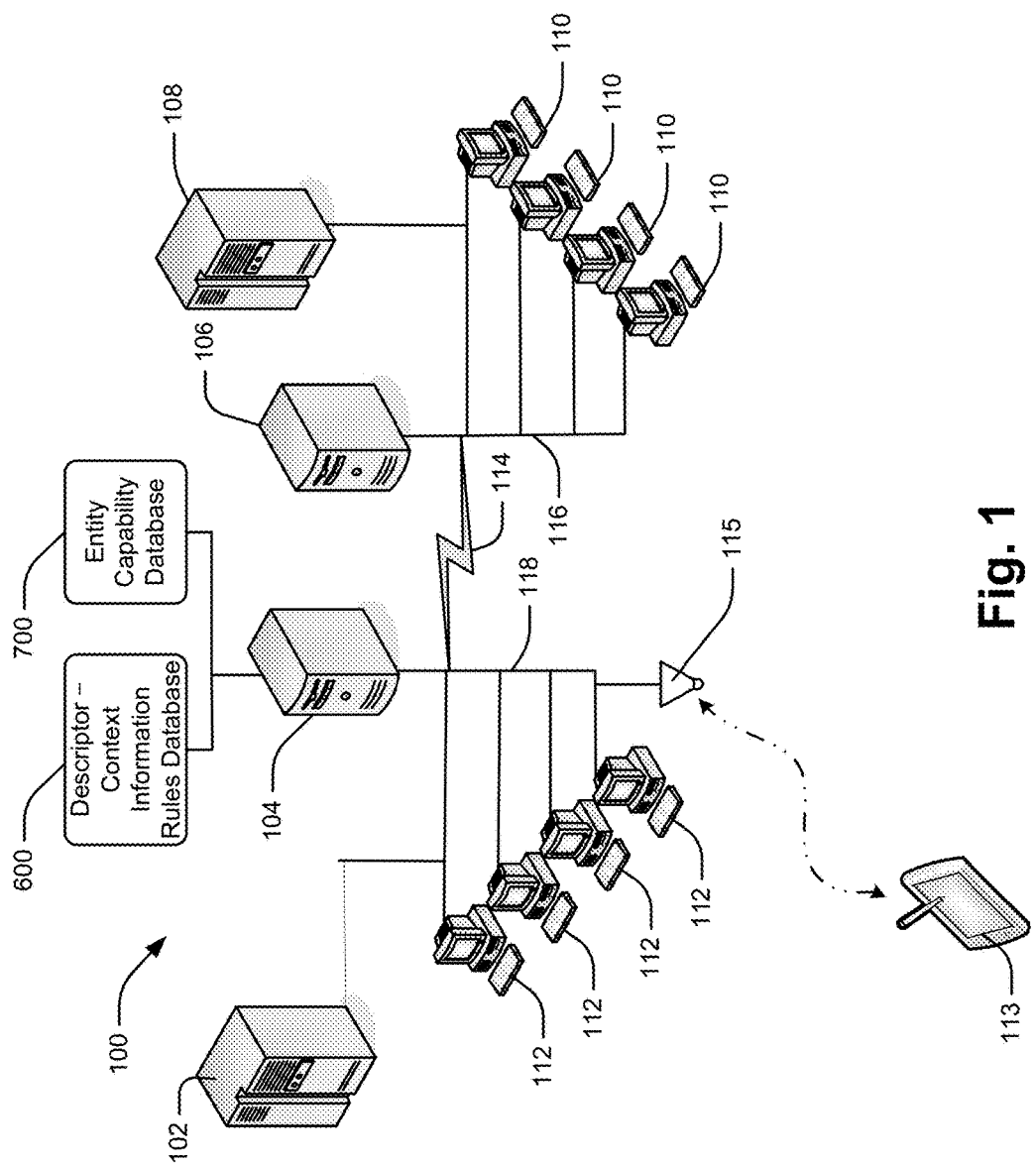
FIG. 1 is an exemplary embodiment of a possible messaging system in accordance with one embodiment of the present invention.

The present invention is directed to a method of communicating messages from one entity to another wherein the first entity does not know the actual identity and/or electronic address of an intended recipient. The messaging may be useful in any situation in which one party refers messages to another such as occur in medical or healthcare, legal, insurance, shipping, inventory management, and other similar fields. For simplicity, the following description uses an example of sending electronic messages between two medical institutions including St. Mary's Hospital ("St. Mary's") and a local healthcare cooperative ("LHC").

In one embodiment, St. Mary's Hospital and LHC have established an inter-institution messaging network 100. The messaging network 120 may connect two or more electronic medical records ("EMR") systems 102 and 108 by a communication network 114. Each institution's EMR system 102 and 108 contains information regarding a patient including contact information, patient medical histories, schedules, visit information, doctors associated with the patient, prescriptions, treatments, emergency contact information, payment information, medical images, and lab results.

The communications network 114 may be implemented across an industry standard network, including the internet, that permits electronic transmission of information from one server to another. In the case of electronic messages between two distinct institutions, the messaging network 100 may comprise at least one messaging or e-mail server 104 and 106 at each of the institutions. The communications network 114, if implemented on the Internet, may be implemented using a virtual private network wherein the two messaging servers are treated as if they are on a private network.

Referring still to FIG. 1, devices 110 and 112 are associated with LHC's and St. Mary's e-mail servers 104 and 106, respectively. Devices 100 and 112 are shown as desktop computers but may be any type of interface devices such as laptops, wireless phones or smart palm type devices, pad type devices, etc. Each interface device can be used to compose and send electronic messages to other devices 110 or 112.

Where a message is sent from one device to another device associated with the same entity (e.g., St. Mary's), the message is routed from the sending device to the e-mail server associated with the entity and out to the target device in most cases without transmission through network 114. For instance, a message from a first device 112 to a second device 112 associated with St. Mary's in FIG. 1 would be routed through server 104 without passing through network 114.

Where a message is sent from one device 112 associated with St. Mary's to another device 110 associated with LCH, the message is routed to St. Mary's e-mail server 104, through network 114 to server 106 which in turn routes the message to the intended recipient address. Here, information in the electronic message assists the sending messaging server 104 to determine where and how to send the electronic message to the receiving messaging server 106. A messaging server 104 or 106 may act as both a sending messaging server and a receiving messaging server.

Hereafter, unless indicated otherwise, the phrase "internal message" will be used to refer to a message sent from one device to another device where the sending and receiving devices are served by a single e-mail server (e.g., 104 or 106). Similarly, the phrase "external message" will be used to refer to a message between devices that are served by different e-mail servers. For instance, a message between one device 112 and another device 110 that are served by servers 104 and 106, respectively, would be an external message.

In one exemplary scenario, a physician using a computer 112 at St. Mary's desires to send an external message to another physician or healthcare professional using a computer 110 at LHC. For example, a first physician enters information regarding a patient visit into St. Mary's EMR system 102 using his or her computer 112 regarding an emergency room visit. The physician then desires to send some or all of the information to the patient's PCP at a local family care clinic run by LHC. It will be appreciated that LHC may be running a different EMR system 108 than St. Mary's (i.e., EMR system 102). It will be further appreciated that even if the two institutions have an EMR system sold by the same vendor, the particular instances and implementations may be separate with separate databases, servers, and patient records. Accordingly, the first physician may not have ready access to either the name of the primary care physician or the electronic message address for the physician.

In accordance with the present invention, the physician at St. Mary's may compose an electronic message using St. Mary's EMR system 102 or e-mail system 104 using computer 112. The electronic message may include an address and a patient identifier. Additional information may be included with an electronic message such as a subject, a return address, a message body, certain header and routing information, and part or all of a patient medical record. The electronic message of the instant invention may be implemented using either common electronic messaging schemes including e-mail (e.g., smtp and imap) or a custom messaging system.

Figure 2A:
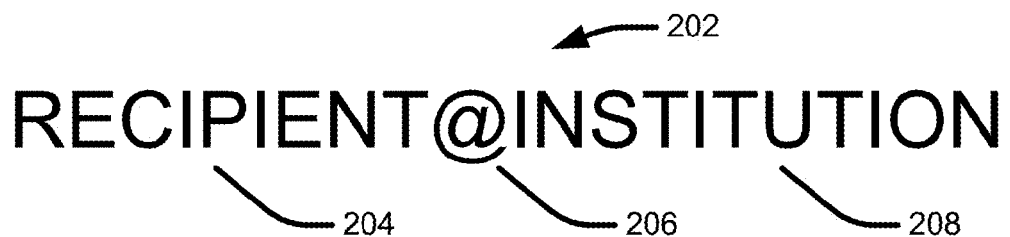
FIGS. 2A-C show exemplary embodiments of possible recipient descriptor addressing schemes.

With reference to FIGS. 2A, an address for an electronic message may be in a form 202 of: recipient@institution. For instance, if the physician knows the name of the patient's primary care physician is Dr. John Smith, the physician could compose the message with an address: john.smith@LHC. In this case, the address is composed of the recipient designation 204 and the institution identifier 208 separated by token 206 indicated by the "@".

Figure 2B:
Figure 2C:
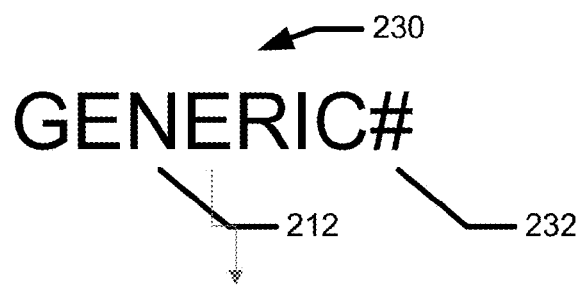

However, when a physician does not know the name of a patient's PCP or does not know the format of an address in the LCH system, as is typically the case for electronic messages sent between two separate institutions, the physician using the electronic messaging system 100 of the present invention can address the message using a generic or general descriptor or identifier 212 and an institution identifier 208 separated by a token 206 as shown in FIG. 2B. For instance, an exemplary descriptor of this type may be PCP@LHC. In this case "PCP" is short for "primary care physician." Similarly, if, instead of the primary care physician, the physician wanted to send a message to the patient's surgeon, the physician could address the message as: surgeon@LHC. Accordingly, the messaging system allows the physician to address electronic messages using one of a set of short descriptive generic "caregiver" type identifiers.

In addition, the addressing function can also be shorthand for intra-institution communications or internal messages. For example, even if the physician could determine a patient's PCP—as either provided by an EMR system or by a patient—the physician can avoid looking up the PCP's address and simply address the electronic message using either generic identifier 212 and institution identifier 208 (e.g., PCP@stmarys) or, even more simply, using generic identifier 212 (e.g., PCP). In the second example, the institution identifier 208, "@stmarys", is implied since the physician is sending the message internally. In this case, the address comprises only the caregiver type descriptor.

Similarly, even if a patient's primary care physician is not part of the St. Mary's EMR system 102, a physician may still be able to address the electronic message by its generic identifier 212 (e.g., as "PCP"). In this case, St. Mary's EMR system 102 may have previously recorded PCP information associated with a patient. This information may include both the name of the patient's PCP and an associated institution. Accordingly, if the EMR system 102 indicates that the patient has a "PCP" at LHC, messages addressed to PCP will be rerouted to "PCP@LHC". This functionality is described in further detail below with respect to the routing of electronic messages using information from the EMR system.

In at least some embodiments, an electronic message also includes a patient identifier. In one embodiment, the patient identifier is simply a numeric or alpha-numeric key that uniquely identifies a patient record in an EMR system. However, under the scenario above, St. Mary's EMR system 102 and LHC's EMR system 108 may not have common, unique patient record identifiers. In this case, one alternative is to create a token that can be included with the electronic message that will be recognized by a receiving messaging server. In this embodiment, a patient may provide the token that can be read and stored by the sender's EMR system. For example, the patient may carry a card with the token represented by a bar code or magnetic strip. The token is read by the physician's system and the token is stored within the electronic message sent from St. Mary's and will be used to identify the patient at LHC's messaging server 106, as further discussed below.

In the case that neither a common, unique identifier or token is available, the patient identifier may include a sufficient amount of contextual identifying information within the electronic message so that the EMR system at the receiving institution can correctly and uniquely identify the patient. For example, the electronic message may include one or more of the following information: first name, last name, date of birth, last four digits of a social security number, mother's maiden name, number of children, and place of birth. There are many possible combinations of information that may be successfully used as a patient identifier. This information can be retrieved from a sending party's EMR system and incorporated into the electronic message as part of the body, the header, or as an attachment. For instance, in at least some embodiments, when a specialist is using an EMR system to view a patient chart and decides to send an e-mail to the patient's PCP upon opening up an e-mail application to compose the message, the system may automatically glean patient identifier information (e.g., a patient identifier) from the currently opened patient chart and add that information to an e-mail field. As another instance, when a specialist is composing an e-mail to a PCP as indicated by entry of "PCP" in an e-mail "To" field, the system may automatically identify the last ten patient charts viewed by the specialist and provide a list of ten patient identifiers for selection by the specialist. Here, upon selection of a patient from the list, a patient identifier would be added to an appropriate e-mail field.

The electronic message may also include a body that contains the message to be delivered. The body can be free form text typed by the sender. It can also be structured text based on a field or fields in the sender's EMR system. In the latter case, for example, the body of the electronic message can be an automated report filled in using information saved in the EMR system by the physician. For example, an Emergency Room physician may send an electronic message comprising a discharge report to a patient's PCP. The discharge report can be a template or form document in which the information regarding the visit can be automatically completed by using values stored in St. Mary's EMR system 102.

In addition, the electronic message may include part or all of an electronic medical record. This information may be copied as text into the body of the electronic message. It can also be attached to the electronic message as a file attachment. It may also be attached as an electronic link. The electronic link provides information for a communications protocol whereby the receiving system can remotely retrieve information from the sender's EMR system.

In the context of an EMR system, it is contemplated that the functions for sending and receiving messages in an electronic messaging system 120 of the present invention may be incorporated directly into the EMR system. In this case, the electronic messaging system 120 has ready access to the patient's medical record information while the messaging is being prepared and before it is sent.

In at least some embodiments, when a sender finishes an electronic message and sends it, the message is provided to the sender's messaging server 104. The sender's messaging server 104 is responsible for routing the message to the recipient's messaging server via the communications network 114. The process of routing may involve obtaining the external address of the recipient's messaging server 106, preparing the electronic message for transmission across the communications network 114, encrypting the electronic message, and actually sending the electronic message.

In the case of an "external" message, (i.e., a message addressed to an entity outside the sender's EMR system 102), the sender's messaging server 104 must determine the address of the external entity by examining the address in the e-mail. In the above example addressed to "PCP@LHC" the sender's messaging server 104 must first determine where and what institution identifier 208, "LHC," means. The sender's messaging server 104 or the sender's EMR system 102 may be programmed so that an "institution" named "LHC" points at the server address of the local health cooperative. This information may be indexed by the name "LHC." The server address may be an internet protocol address ("IP" address) or other uniform resource indicator ("URI") that includes protocol, IP address, and port number and other communication information. The server address could also be an internet domain such as "localhealthcooperative.org." If the institution is found, the message is routed using an appropriate communications protocol. If no institution is found, then the messaging server may return the message to the sender. The return message may include information that no such institution is found. Alternatively, or in addition to returning the message to the sender, the message could be sent to an assistant or other specialist at the sender's institution for proper addressing information.

In addition, as noted above, another embodiment of the present invention might have a situation in which the sender addresses a message without an institution identifier 208 (e.g., "PCP"), where the sender's EMR system 102 has a record in a patient chart indicating that the generic identifier "PCP" is, in fact, an external entity. In this case, upon retrieving the destination information for "PCP" from the patient record for the patient matching the patient identifier, the message is rerouted by the sending messaging server 104 using the proper institution. For example, if the EMR system 102 identifies that a PCP is at LHC, then the message is not delivered internally, but the address is changed to "PCP@LHC" and resent. Alternatively, if the EMR system 102 has the complete address for the primary care physician, Dr. John Smith having an address john.smith@ localhealthcooperative.org, then the message can be sent directly to that address avoiding additional processing by both the sending EMR system 102 and receiving EMR system 108.

With respect to both internal messaging and the situation in which a sending EMR system 102 contains some or all of the relevant contact information, the sender user interface can implement the appropriate addressing queries directly. For example, as the Emergency Room physician types "PCP" into the address field of a message composition screen on computer 112, the user interface software can search the EMR system 102 for any corresponding record. As discussed above, a message may be composed in the context of a patient record and, therefore, the messaging system 100 may have ready access to information in the EMR system 102. Accordingly, the user interface software can pass both the generic identifier "PCP" and a patient identifier directly to the EMR system 102 in order to retrieve the corresponding results. If the EMR system 102 returns the destination address of john.smith@localhealthcooperative.org, for example, then the address of "PCP" can be replaced with john.smith@localhealthcooperative.org.

In the context of an "external" message, the sending messaging server 104 is responsible for sending the electronic message across the communications network 114 to the receiving messaging server 106. Upon receiving the message, the receiving messaging server 106 will first determine the proper recipient of the electronic message. It will be appreciated that "PCP" or "doctor" or "surgeon" and other caregiver types potentially identify a large number of users of the receiving institution's EMR system 108, but only a few or perhaps one will be associated with a particular patient. Accordingly, a system of the present invention may select from among all the possible recipients only those that correspond to the patient identifier. In other words, the combination of caregiver type and the patient identifier will select a subset of all possible caregivers at a receiving institution. As a result, a select group of all users of the corresponding caregiver type is set as the actual intended recipient(s). So, for example, if there are 1000 doctors that are in the category of "primary care physician" at LHC, and the patient has only one primary care physician, then the electronic message addressed to PCP@LHC for this patient will be delivered only to the one designated primary care physician, not every primary care physician.

In one embodiment, a receiving messaging server 106 will query the EMR system 108 for the address information of the caregiver corresponding to both the patient identifier and the caregiver type. In the case that the patient identifier is a token or a common, unique identifier, the patient record may be retrieved directly from the EMR system 108. In the case that the electronic message only includes patient information, the receiving messaging server 108 uses some or all of the supplied patient information in the electronic message to identify a single patient in the receiving messaging server's 106 EMR system 108. In any case, if a patient record is successfully retrieved and a corresponding caregiver is found, then the message is routed, by the receiving messaging server 106, to the intended recipient's computer 110.

In a possible embodiment, the receiving messaging server 106 may also return to the sending messaging server 104 an acknowledgement that the message was successfully received. The acknowledgement may also include the address information of the intended recipient. The sending messaging server 104 then may use the information in the acknowledgement to update its own EMR system 102. In this case, any future messages to the patient's primary care physician, for example, can be routed directly to the PCP without requiring additional processing by the receiving messaging server 106. The acknowledgement itself may also be sent directly to the sender or saved to the EMR system 102 for future reference.

If, however, the receiving messaging server 106 cannot find either a corresponding patient or a corresponding caregiver, an undeliverable message may be returned to the sending messaging system 104. Similarly, if the receiving messaging server 106 is unable to identify a single patient from the receiving messaging server's EMR system 108, the receiving messaging server 106 may also return an undeliverable message. In the latter case, it will be understood that both the sending and receiving institutions may want to guard a patient's privacy and, thus, it may be inappropriate to send a message to more than one patient. The sending messaging server 104 can forward the undeliverable message to the sender for additional action. In some embodiments, the undeliverable message may include which information failed: i.e., "no such patient," "no such caregiver," "patient no longer member of this institution," etc.

Alternatively, instead of or in addition to returning an undeliverable message, the receiving messaging server 106 may also query its own EMR system 108 for additional information. For example, if the EMR system 108 contains a record for the patient but notes that the primary care physician is at another institution, then the receiving messaging server 106 can return such information to the sending messaging server 106. In addition, the receiving messaging server could reroute the electronic message to the correct institution using the messaging system.

The system of the present invention also contemplates more complicated routing routines for use with generic caregiver types. The generic caregiver types could include things like "specialist" or "surgeon" or "nurse." In the case of specialist, any particular hospital or medical system could have hundreds of types of specialists: cardiac, pulmonary, ENT, endocrinology, anesthesiology, podiatry, etc. Such naming conventions may be inconsistent as between institutions and the address information may not be readily apparent or accessible for a user attempting to send a message. A system in accordance with the present invention can use information present in the associated medical records to correctly select an intended message recipient from among all of the specialists. For example, if the patient were admitted to St. Mary's Emergency room for complications related to a patient's diabetes, the Emergency Room physician may want to send a message to the patient's endocrinologist at LHC. However, instead of writing "endocrinologist@LHC" the emergency room physician can simply type an address such as "specialist@LHC." In this case, the electronic message further contains information regarding the admission to the emergency room regarding diabetes. Such information could include the fact of the visit, vital medical information, the problem, and the medicine or treatments prescribed, and other customary information. The receiving messaging server 106 then could use the "problem," or such other appropriate indicator, identified as "diabetes complications" to select a patient's diabetes specialist from among all of a patient's specialists.

In another embodiment, the caregiver type may be associated with more than one recipient. For example, in the endocrinologist example above, the specialist for endocrinology may also be associated with the patient's diabetes nurse educator, nutritionist, and primary care physician. In this case, when the receiving messaging server 106 queries the EMR system 108 for the diabetes specialist, more than one recipient is returned. The message may then be forwarded to all of the recipients in at least some embodiments. Similarly, in the case of a surgery or other similar event, a message directed to "surgeon" or "surgery" and referencing a particular operation may be delivered to all or a subset of the people associated with that surgery, e.g, a surgeon, a surgical assistant, an anesthesiologist, etc.

In still other cases, a list of possible patient specific possible intended recipients may be automatically provided for a physician to choose from. For instance, when "specialist" is entered in an address field, the inventive system may identify a list of five different specialists associated with a patient that is associated with the message being composed. Here the list of five specialists is provided, and one or more may be chosen as intended recipients. Upon selection, recipient addresses are used to replace the "specialist" designation.

A similar result is possible for ordering labs, medical images or prescriptions. In the case of a pharmacy, a physician can use an electronic message to deliver prescriptions or instructions to the patient's designated pharmacy. In this case, addressing a message to "pharmacy" or "pharmacy@LHC" can route message information to the patient's designated pharmacist. In some cases, if special approval is needed, the receiving messaging system could determine that, not only should the designated pharmacy/pharmacist receive the message, but that the patient's PCP should receive a message in order to maintain the primary care physician's EMR system updated.

In another embodiment of the present invention, the electronic message may also include part or all of a patient's electronic medical record from the sender's EMR system 102. The receiving messaging server 106 can then incorporate that information into its own EMR system 108. For example, if the Emergency Room physician attached a visit record from the emergency room visit to an electronic message, the receiving messaging server 106 may desire to incorporate information regarding that visit into its own EMR system 108. It could, for example, record information about the fact of the visit, the date of the visit, the problems, the doctor, the treatment and any corresponding prescriptions directly into its own electronic medical records. In one embodiment, this information will be included automatically. In another embodiment, only certain portions of the medical record will be incorporated into the receiving messaging system's 106 EMR system 108.

Furthermore, the electronic message may include additional attachments or documents that the receiving messaging system may wish to retain in its own medical records system. For example, if the sending institution is a radiology clinic and the electronic message is sent to the primary care physician, the electronic message may include copies of x-rays or MRI scans. In one embodiment, the electronic message could identify such attachments accordingly, and the receiving messaging system may automatically store such documents to the corresponding location in its own EMR system. In addition, in order to prevent duplication of images, the receiving messaging system could strip the attachments from the electronic message before forwarding the messages to the intended recipients and include, rather than a complete image file, a link to the location in the EMR system.

In another embodiment, the electronic message, its contents and attachments, or any combination thereof may be encrypted by the sending messaging server. In order to protect patient privacy and patient medical and health information, the electronic message may be encrypted using one or more forms of known encryption methods. In one possible embodiment, the sending and receiving messaging servers have a shared encryption key. If a messaging server can send messages to more than one other messaging server, the messaging server may store different encryption keys for each of the messaging servers with which it can communicate. The sending messaging server then, before sending the electronic message, can encrypt the electronic message using the shared encryption key. The information is then transmitted to the receiving messaging server. The receiving messaging server then can retrieve the shared encryption key associated with the sending messaging server and decrypts the electronic message.

Each messaging server 104 or 106 may be a general purpose computer server. The computer server includes a receiving means for receiving an electronic message and a sending means for forwarding the electronic message to its intended recipient or recipients. The receiving means comprises a processor and memory unit for executing a software program or algorithm to receive an electronic message. The receiving means may further include a network connection for connecting to the communications network. The networking connection may be a network card that is connected to the communications network. In the alternative, the receiving means may comprise a communicative link to a database system or EMR system for receiving a message sent internally. The software is programmed to accept incoming electronic message. The software may be an industry standard e-mail software server running an industry standard e-mail protocol such as SMTP or IMAP. Alternatively, the software program may be a messaging system integrated with the EMR system for exchanging messages. This software program may be implemented so as to monitor the communications network for traffic on a specific port.

The sending means comprises a processor and memory unit for executing a software program or algorithm to send an electronic message. It may also further comprise a network connection for the purpose of sending electronic message external to the messaging system. The network connection may be a networking card connected to the communications network. In the alternative, the sending means may comprise a communicative link to a database system or EMR system for storing a message sent internally. The software may be an industry standard e-mail software server running an industry standard e-mail protocol such as SMTP or IMAP. Alternatively, the software program may be a messaging system integrated with the EMR system for exchanging messages. This software program may be implemented so as to monitor the communications network for traffic on a specific port.

The messaging system further comprises a patient record retrieving means. The patient record retrieving means comprises a processor, memory unit and a communicative link to a disk. The disk may be located locally on the messaging system or at a remote database or EMR system. Accordingly, the communicative link may be a physical connection with the messaging system, a network connection, or a high speed device connection (firewire, USB, or similar). The disk stores one or more patient records. The messaging system is programmed to retrieve patient records from the disk using standard database operations or disk operations. For instance, if the disk has a relational database, the messaging system is programmed to query the database using the patient identifier to retrieve the corresponding patient record.

The messaging system further comprises a caregiver record retrieving means. The caregiver record retrieving means comprises a processor, a memory unit and a communicative link to a disk. The disk may be located locally on the messaging system or at a remote database or EMR system. Accordingly, the communicative link may be a physical connection with the messaging system, a network connection, or a high speed device connection (firewire, USB, or similar). The disk stores one or more caregiver records. As with the patient record retrieving means, the messaging system is programmed to retrieve caregiver records from the disk using standard database operations or disk operations. For instance, if the disk has a relational database, the messaging system is programmed to query the database using the patient identifier and the caregiver type to retrieve the corresponding patient record.

Figure 3:
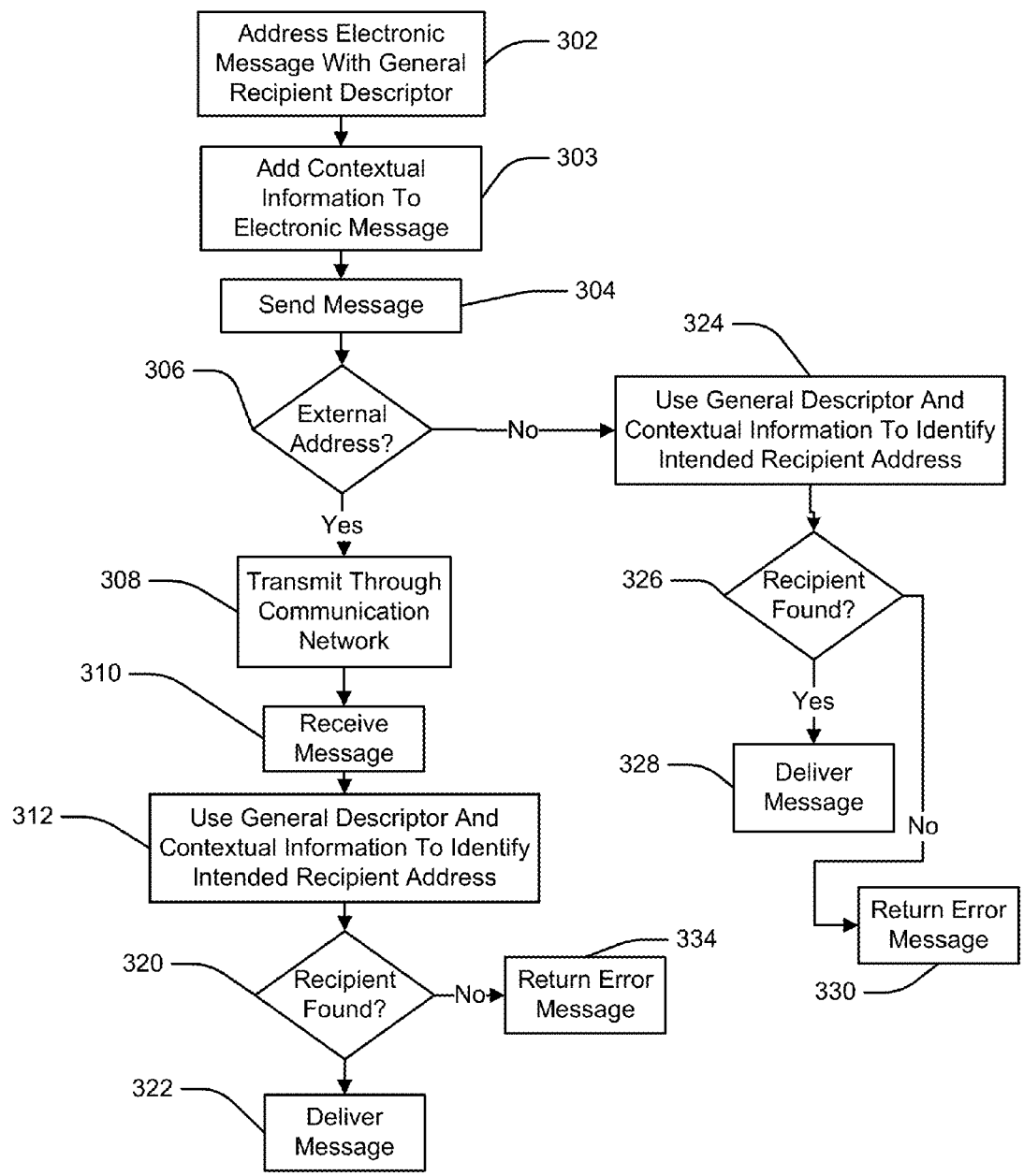
FIG. 3 is a flowchart showing one possible workflow for sending and receiving an electronic message in accordance with one embodiment of the present invention.

Referring now to FIG. 3, an exemplary flow chart showing one work flow for sending and receiving electronic messages in accordance with at least one embodiment of the present invention illustrated. Referring also to FIG. 1, at block 302, a caregiver may compose an electronic message using one of the messaging servers 104 in which the caregiver addresses the intended recipient using one of the general recipient descriptors (e.g., PCP). At block 303 the messaging server 104 automatically adds contextual information to the electronic message. Here, again, for example, the contextual information may include a patient identifier or some other type of information that may be useful in resolving which of several PCPs to which the electronic message should be transmitted. In the alternative, the message may already include contextual information. At block 304 the caregiver selects a send icon or the like to send the electronic message to a recipient.

Referring still to FIGS. 1 and 3, at decision block 306, the messaging server 104 determines whether or not the message is targeted to an external recipient or an internal recipient serviced by server 104. Where the message is intended for an internal recipient, control passes to block 324 where messaging server 104 uses the general descriptor and contextual information to identify an intended recipient address. At block 326, if no recipient is found, control passes to block 330 where an error message is returned to the physician indicating that no intended recipient address has been identified. At block 326, when a recipient is found, control passes to block 328 where the electronic message is delivered to an electronic address associated with the intended recipient.

Referring once again to decision block 306, where the message is intended for an external recipient, control passes to block 308 where the message is transmitted through a communication network (see 114 in FIG. 1) to a second messaging server 106 associated with the external address. After the message is received at the second messaging server 106 at block 310, control passes to block 312 where the receiving server uses the general descriptor and contextual information to identify an intended recipient address. Once an intended recipient address has been identified at block 320, control passes to block 322 where the message is delivered to the intended recipient via the address. Where no recipient is identified by block 320, control passes to block 334 where an error message is returned.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, the invention is to cover any case where a general recipient descriptor is associated by a message composer (e.g., a caregiver) with an electronic message and contextual information is associated with the message where the general recipient descriptor and contextual information are then used to automatically resolve one or a small subset of intended message recipients irrespective of which of several servers in a networked system performs the resolving process. For instance, as indicated above, a server used to compose an e-mail may resolve an intended recipient if the server has sufficient information. As another instance, a messaging server receiving an electronic message including the general recipient descriptor and contextual information may resolve the intended recipient. EMR systems may help resolve intended recipients as well.

As another example, in at least some embodiments it is contemplated that a first server used to compose a message may communicate with a second server after a general recipient descriptor is provided (e.g., entered in an e-mail address field) and before the electronic message is sent or even finally composed where the second server can resolve an intended recipient and provide the recipient's address back to the first server to be used during subsequent transmission of the electronic message. Here, for instance, after "PCP@LHC" is specified by a physician, a first server may glean patient identifier information and send a pre-e-mail to the LHC EMR system to retrieve an intended recipient address. The LHC EMR system uses the general recipient descriptor PCP and patient identifier to identify an address for the patient's PCP which is transmitted back to the first server. The first server can either present the intended recipient address to the physician for selection or automatically replace the "PCP@LHC" descriptor with the intended recipient address.

Moreover, in some cases an affirmation step may be required where, after a general recipient descriptor is entered into an address field and prior to transmitting a message intended for a recipient, the inventive system uses the descriptor and contextual information associated with the message to identify a likely intended recipient and presents the recipient for selection by the message composer as opposed to automatically replacing the descriptor with the recipient's address. Here, the affirmation requirement is an added step which should minimize the possibility of a message being inadvertently transmitted to an incorrect or unintended recipient.

In still other cases, when a message composer selects a send icon to send a message to a recipient identified via a general descriptor (e.g., PCP), the system may first resolve a likely intended recipient and provide a recipient identifier (e.g., a caregiver's name) for selection prior to transmission, again requiring an affirmative selection of the specific recipient prior to transmission.

As one other example, while patient identifiers or patient information is described above as the contextual information used to resolve an intended recipient along with a general recipient descriptor, other embodiments may use other types of contextual information from a patient chart or the like. For instance, a medical facility may have a children's hospital that specializes in treating children under the age of thirteen. Here, when a PCP designates ENT as a recipient descriptor in an e-mail associated with a child, the system may automatically glean the child status from the patient's chart and select an ENT specialist at the facility that works in the children's hospital as the intended recipient for the message.

As still another example, contextual information may be related to the geographic location of a system that receives an electronic message. For instance, where a user composes an electronic message at a first system and specifies "GI 58944" as the recipient, the system may use the recipient indication to identify a GI specialist nearest the zip code 58944 as the intended recipient and may therefore complete the message address with an address targeting the intended recipient.

As another example, an intended recipient need not be a single individual and instead may be a group of individuals associated with a single target or recipient address. For instance, in the above example where a recipient indicator is "GI 58944", the recipient address may be a general address for a GI group closest to the specified zip code, effectively delivering the message to all of the members of the group.

Furthermore, as indicated above, the inventive system may be used in many other industries.

Accordingly, the scope of the invention should be determined from the following claims and not limited by the above disclosure.

I claim:

1. A computer-implemented electronic messaging method comprising the steps of:
   receiving an electronic message at a first system, the electronic message comprising a general recipient descriptor indicating a healthcare provider type of an intended healthcare provider recipient of the electronic message, the general descriptor being different from an intended recipient address for the intended healthcare provider recipient, and the electronic message, as received, not including the intended recipient address for the intended healthcare provider recipient;
   obtaining contextual information associated with the electronic message at the first system;
   querying an electronic medical record system to identify a plurality of healthcare provider recipients corresponding to the general recipient descriptor at the first system,
   identifying the intended recipient address for the intended healthcare provider recipient of the electronic message from the plurality of healthcare provider recipients, based upon the the contextual information; and
   after identifying the intended recipient address, delivering the electronic message to the intended healthcare provider recipient at the intended recipient address.

2. The computer-implemented electronic messaging method of claim 1 wherein the contextual information comprises a patient identifier comprises a token included in the electronic message.

3. The computer-implemented electronic messaging method of claim 1 wherein the contextual information identifies a patient identifier is retrieved from a patient chart.

4. The computer-implemented electronic messaging method of claim 3 wherein the patient chart is the patient chart most recently accessed by a healthcare provider composing the electronic message.

5. The computer-implemented electronic messaging method of claim 1 further comprising the step of acquiring contextual information from information in the electronic message.

6. The computer-implemented electronic messaging method of claim 1 wherein the contextual information comprises a patient chart associated with the electronic message.

7. The computer-implemented electronic messaging method of claim 1 wherein the step of receiving an electronic message at a first system includes composing the electronic message at the electronic medical records system and transmitting the electronic message to the first system.

8. The computer-implemented electronic messaging method of claim 1 wherein the electronic message is composed using the first system.

9. The computer-implemented electronic messaging method of claim 1 wherein the electronic message is composed using a second system separate from the first system and wherein the step of receiving the electronic message includes receiving the electronic message from the second system at the first system.

10. The computer-implemented electronic messaging method of claim 1 wherein the specialist includes one or more of a cardiac specialist, an ear, nose, and throat specialist, a pulmonary specialist, an endocrinology specialist, an anesthesiology specialist, and a podiatry specialist.

11. The computer-implemented electronic messaging method of claim 1 wherein the general recipient descriptor further indicates a healthcare location associated with the intended healthcare provider recipient, wherein the healthcare location includes one or more of a hospital, a healthcare cooperative, an emergency room, a surgery department, a pharmacy, and a laboratory; and
   wherein the intended recipient address for the intended healthcare provider recipient of the electronic message is identified based upon the healthcare location as well as the healthcare provider type and the contextual information.

12. The computer-implemented electronic messaging method of claim 1, further comprising the step of automatically inserting the intended recipient address in an address field in the electronic message.

13. The computer-implemented electronic messaging method of claims 1, further comprising the step of presenting the intended recipient address for selection as a target address for the electronic message.

14. The computer-implemented electronic messaging method of claim 1 wherein the step of using the healthcare provider type and the patient identifier to identify the intended recipient address for the intended healthcare provider recipient of the electronic message includes using the healthcare provider type and the patient identifier to identify at least two intended recipient addresses for intended healthcare provider recipients of the electronic message.

15. The computer-implemented electronic messaging method of claim 1, further comprising the steps of providing contextual information in the message and evaluating contextual information to identify a geographic information associated with the location of the first system.

16. The computer-implemented electronic messaging method of claim 2, further comprising the step of providing a token on a card carried by the patient and reading the token into the electronic medical records system.

\* \* \* \* \*

UNITED STATES PATENT AND TRADEMARK OFFICE
CERTIFICATE OF CORRECTION

PATENT NO. : 10,446,267 B2
APPLICATION NO. : 15/443553
DATED : October 15, 2019
INVENTOR(S) : David E. Fuhrmann Page 1 of 1

It is certified that error appears in the above-identified patent and that said Letters Patent is hereby corrected as shown below:

In the Claims

Column 17, Claim 13, Line 9, "claims" should be --claim--.

Signed and Sealed this
Nineteenth Day of November, 2019

Andrei Iancu
*Director of the United States Patent and Trademark Office*